United States Patent [19]

Faulkner et al.

[11] Patent Number: 5,665,390
[45] Date of Patent: Sep. 9, 1997

[54] STABILIZED TABLET FORMULATION

[75] Inventors: Patrick Gerard Faulkner, Collegeville; Mark Warren Fisher, King of Prussia, both of Pa.; Joseph Peter Sauer, Cleminton; Carlos Roberto Hernandez, Pensauken, both of N.J.

[73] Assignee: SmithKline Beecham Corporation, Philadelphia, Pa.

[21] Appl. No.: 451,790

[22] Filed: May 26, 1995

Related U.S. Application Data

[63] Continuation of PCT/US94/09945, May 11, 1995.

[30] Foreign Application Priority Data

Sep. 3, 1993 [GB] United Kingdom ............... 9318348
Nov. 19, 1993 [GB] United Kingdom ............... 9323864
Jun. 14, 1994 [GB] United Kingdom ............... 9411903

[51] Int. Cl.$^6$ ............... A61K 31/56; A61K 31/575; A61K 9/20; A61K 47/12
[52] U.S. Cl. ............... 424/465; 514/177; 514/178; 514/179; 514/182; 514/772; 514/784; 514/960; 514/970
[58] Field of Search ............... 424/465; 514/177–182, 514/784, 960, 970

[56] References Cited

U.S. PATENT DOCUMENTS

| | | | |
|---|---|---|---|
| 4,159,326 | 6/1979 | Barton et al. | 424/235 |
| 4,172,132 | 10/1979 | Draper et al. | 424/243 |
| 4,185,101 | 1/1980 | Draper et al. | 424/243 |
| 4,473,564 | 9/1984 | de Winter et al. | 424/238 |
| 5,017,568 | 5/1991 | Holt et al. | |
| 5,212,166 | 5/1993 | Panzeri et al. | |

FOREIGN PATENT DOCUMENTS

| | | |
|---|---|---|
| 0 173 478 | 3/1986 | European Pat. Off. |
| 0 465 141 A1 | 1/1992 | European Pat. Off. |
| 0 465 141 A2 | 1/1992 | European Pat. Off. |
| 0 567 271 A2 | 10/1993 | European Pat. Off. |
| WO91/13550 | 9/1991 | WIPO |
| WO92/00010 | 1/1992 | WIPO |
| WO93/19758 | 10/1993 | WIPO |

*Primary Examiner*—Shep K. Rose
*Attorney, Agent, or Firm*—Wayne J. Dustman; Charles M. Kinzig; Edward T. Lentz

[57] ABSTRACT

Invented are stabilized tablet formulations of substituted 3,5-diene steroidal compounds. Also invented are methods of preparing stabilized tablet formulations of substituted 3,5-diene steroidal compounds.

2 Claims, No Drawings

STABILIZED TABLET FORMULATION

This application is a continuation of PCT/US94/09945 filed May 11, 1995.

The present invention relates to novel stabilized tablet formulations of substituted 3,5-diene steroidal compounds containing a 3 position electron-withdrawing group and methods of preparing stabilized table formulations of substituted 3,5-diene steroidal compounds containing a 3 position electron-withdrawing group. Preferably, this invention relates to novel stabilized tablet formulations of substituted 3,5-diene sterodial compounds containing a 3 position acid group and methods of preparing stabilized tablet formulations of substituted 3,5-diene steroidal compounds containing a 3 position acid group. Preferably, this invention relates to novel stabilized table formulations of substituted 3,5-diene steroidal compounds containing a 3 position carboxylic acid group and methods of preparing stabilized tablet formulations of substituted 3,5-diene steroidal compounds containing a 3 position carboxylic acid group. Advantageously, the substituted 3,5-diene steroidal compound for use in the presently invented stabilized tablet formulations and presently invented methods is N-t-butyl-androst-3,5-diene-17β-carboxamide-3-carboxylic acid.

DETAILED DESCRIPTION OF THE INVENTION

Novel substituted 3,5-diene steroidal compounds containing a 3 position electron-withdrawing group have recently been shown to exhibit significant pharmaceutical activity. Specifically, said compounds have been found to inhibit steroid 5-α-reductase and are thereby useful in the treatment of prostate diseases such as benign prostatic hypertrophy. Stabilized tablet formulations of substituted 3,5-diene steroidal compounds containing a 3 position electron-withdrawing group are advantageous in preparing dosage units for oral administration.

By the term "substituted 3,5-diene steroidal compound" as used herein is meant a compound of the figure

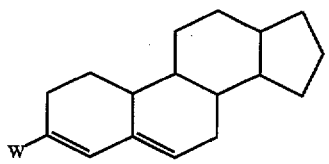

wherein W is an electron-withdrawing group; and the $C_1$ and $C_2$ positions and the $C_8$ to $C_{19}$ positions are optionally substituted with pharmaceutically acceptable substituents, degrees of unsaturation or a combination of pharmaceutically acceptable substituents and degrees of unsaturation.

The term "electron-withdrawing group" is well known to those of skill in the art and is used herein as its standard meaning which is a functional group that draws electrons to itself more than a hydrogen atom would if it occupied the same position in the molecule, as described in J. March, *Advanced Organic Chemistry*, third edition, Pub: John Wiley & Sons, Inc. (1985). Preferred electron-withdrawing groups for use in the presently invented stabilized tablet formulations and presently invented methods are: —COOH, —P(O)(OH)$_2$, —PH(O)OH, —SO$_3$H, —CHO, —CONHSO$_2$R$^{20}$ where R$^{20}$ is an alkyl group having from 1 to 6 carbon atoms, —CN, —CONH$_2$ and, where appropriate, esters thereof.

By the term "acid group" as used herein is meant a substituent selected from the group consisting of: —COOH, —P(O)(OH)$_2$, —PH(O)OH and —SO$_3$H.

The most preferred electron-withdrawing group for use in the presently invented stabilized tablet formulations and present invented methods is —COOH.

By the term "fatty acid" as used herein is meant saturated and unsaturated fatty acids of the standard usage wherein the compound contains from about 10 to 22 carbon atoms, preferably decanoic acid, stearic acid, palmitic acid, oleic acid, lauric acid or myristic acid; most preferably, stearic acid.

Preferred substituted 3,5-diene steroidal compounds for use in the presently invented stabilized tablet formulations and presently invented methods include compounds of the Formula I

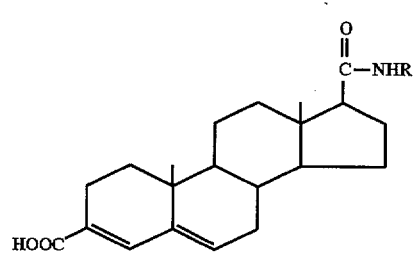

wherein R is a hydrocarbon radical selected from substituted or unsubstituted 1- or 2-adamantyl, 1-, 2- or 7-norbornanyl.

Included within the scope of compounds of Formula I are those wherein the 1- or 2-adamantyl or 1-, 2- or 7-norbornanyl moieties are substituted with one or more of: $C_1$–$C_4$ linear or branched alkyl; nitro; oxo; $C_7$–$C_9$arylalkyl, including benzyl; $(CH_2)_n COOR^1$ where n is 0–2 and $R^1$ is H or linear or branched $C_1$–$C_4$ alkyl; $CH_2OH$; OH; $OR^2$ where $R^2$ is $C_1$–$C_4$ linear or branched alkyl; halo; $CONH_2$; $CH_2NH_2$; $CH_2NHCOR^3$ where $R^3$ is $C_1$–$C_4$ linear or branched alkyl; phenyl and p-substituted phenyl wherein the substituents are members selected from the group consisting of nitro; amino; sulfo and cyano.

Compounds of Formula I and methods of preparing compounds of Formula I are described in EPO Publn. No. 0465141 (Published 8 Jan. 1992) to Rasmusson, et al. (Merck Co. Inc.). Said compounds are disclosed therein as being useful in inhibiting steroid 5-α-reductase.

Preferred substituted 3,5-diene steroidal compounds for use in the presently invented stabilized tablet formulations and presently invented methods include compounds of the Formula II

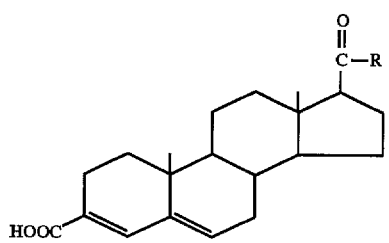

wherein R is $C_1$–$C_6$ linear or branched alkyl; $C_3$–$C_8$cycloalkyl, which can be substituted with $C_1$–$C_4$alkoxy or $C_1$–$C_4$ linear or branched alkyl; $C_6$–$C_{12}$aryl, which can be substituted with one or more of: —OH, —OC$_1$–C$_4$alkyl, $C_1$–$C_4$alkyl, —(CH$_2$)$_m$OH, —(CH$_2$)$_n$COOH, including protected —OH, where m is 1–4 and n is 1–3.

Additionally preferred substituted 3,5-diene steroidal compounds for use herein are the ketone reduction products of II, the secondary alcohols of the formula wherein R is $C_1$-$C_6$ linear or branched alkyl; $C_3$-$C_8$cycloalkyl, which can be substituted with $C_1$-$C_4$alkoxy or $C_1$-$C_4$ linear or branched alkyl; $C_6$-$C_{12}$aryl, which can be substituted with one or more of: —OH, —$OC_1$-$C_4$alkyl, $C_1$-$C_4$alkyl, —$(CH_2)_m$OH, —$(CH_2)_n$COOH, including protected —OH, where m is 1–4 and n is 1–3.

Compounds of Formula II and the ketone reduction products of II and methods of preparing compounds of Formula II and the ketone reduction products thereof are described in EPO Publn. No. 0465142 (published 8 Jan. 1992) to Rasmusson, et al. (Merck & Co. Inc.). Said compounds and ketone reduction products thereof are disclosed therein as being useful in inhibiting steroid 5-α-reductase.

Particularly preferred substituted 3,5-diene steroidal compounds for use in the presently invented stabilized tablet formulations and presently invented methods include compounds of the Formula III in which;
$R^2$ is H or $CH_3$ and
$R^3$ is
(1) α-hydrogen, α-hydroxyl, or α-acetoxy and/or
(a)

$$\beta\text{-W}-\overset{\overset{\displaystyle O}{\|}}{C}-R^4$$

where W is a bond or $C_{1-12}$alkyl, and $R^4$ is
(i) hydrogen,
(ii) hydroxyl,
(iii) $C_{1-8}$alkyl,
(iv) hydroxy $C_{1-8}$alkyl,
(v) $C_{1-8}$alkoxy,
(vi) $NR^5R^6$, where $R^5$ and $R^6$ are each independently selected from hydrogen, $C_{1-8}$alkyl, $C_{3-6}$cycloalkyl, phenyl; or $R^5$ and $R^6$ taken together with the nitrogen to which they are attached represent a 5–6 membered saturated ring comprising up to one other heteroatom selected from oxygen and nitrogen, or
(vii) $OR^7$, where $R^7$ is hydrogen, alkali metal, $C_{1-18}$alkyl, benzyl, or
(b) β-Alk-$OR^8$, where Alk is $C_{1-12}$alkyl, and $R^8$ is
(i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl,
(2) =CH—W—CO—$R^4$ or =CH—W—$OR^8$, where W is a bond or $C_{1-12}$alkyl and $R^4$ and $R^8$ have the same meaning as above and $R^8$ also is hydrogen or $C_{1-20}$alkylcarbonyl;
(3)

where the dashed bond replaces the 17-α-hydrogen,
(4) α-hydrogen and β-NHCOR$^9$ where $R^9$ is $C_{1-12}$alkyl or β-$NR^5R^6$ where $R^5$ and $R^6$ have the same meaning as above,
(5) α-hydrogen and β-cyano,
(6) α-hydrogen and β-tetrazolyl, or
(7) keto.

Compounds of Formula III and methods of preparing compounds of Formula III are described in U.S. Pat. No. 5,017,568. Said compounds are disclosed therein as being useful in inhibiting steroid 5α-reductase.

Particularly preferred substituted 3,5-diene steroidal compounds for use in the presently invented stabilized tablet formulations and presently invented methods include compounds of the formula (IV)

wherein
Y is oxygen or sulphur;
$R_1$ is methyl, ethyl, isopropyl, tert-butyl, cyclohexyl; and the group $R^3$ is;

Compounds of formula IV and methods of preparing compounds of formula IV are described in U.S. Pat. No. 5,212,166. Said compounds are disclosed therein as being useful in inhibiting steroid 5α-reductase.

Particularly preferred substituted 3,5-diene steroidal compounds for use in the presently invented stabilized tablet formulations and presently invented methods include compounds of the formula (V)

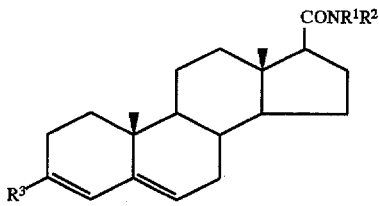

(V)

wherein:

R¹ represents: a hydrogen atom; an alkyl group having from 1 to 6 carbon atoms; or a substituted alkyl group having from 1 to 6 carbon atoms and having at least one substituent selected from aryl groups as defined below and aromatic heterocyclic groups as defined below;

R² represents:

a substituted alkyl group having from 1 to 6 carbon atoms and having at least one substituent selected from aryl groups as defined below and aromatic heterocyclic groups as defined below, and said alkyl group further optionally having a single hydroxy or carboxy substituent; or a diarylamino group in which the two aryl parts are the same or different and each is as defined below;

R³ represents a carboxy group or a group of formula —CONHSO₂R⁴ wherein R⁴ represents an alkyl group having from 1 to 6 carbon atoms;

said aryl groups are carbocyclic aromatic groups having from 6 to 14 ring carbon atoms and which are unsubstituted or are substituted by at least one substituent selected from substituents A, defined below;

said aromatic heterocyclic groups have 5 or 6 ring atoms of which from 1 to 3 are hetero-atoms selected from nitrogen, oxygen and sulphur hetero-atoms and the remainder are carbon atoms, said group being unsubstituted or being substituted by at least one substituent selected from substituents B, defined below;

said substituents A are selected from: alkyl groups having from 1 to 6 carbon atoms; alkoxy groups having from 1 to 6 carbon atoms; alkoxycarbonyl groups having from 2 to 7 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; aromatic acylamino groups in which the aromatic part is a carbocyclic aryl group which has from 6 to 10 ring carbon atoms and which is unsubstituted or is substituted by at least one substituent selected from substituents C, defined below; cyano groups; nitro groups; and carboxy groups;

said substituents B are selected from: alkyl groups having from 1 to 6 carbon atoms; alkoxy groups having from 1 to 6 carbon atoms; hydroxy groups; halogen atoms; carbocyclic aryl groups which have from 6 to 10 ring carbon atoms and which are unsubstituted or are substituted by at least one substituent selected from substituents C, defined below; amino groups; alkylamino groups having from 1 to 6 carbon atoms; dialkylamino groups in which each alkyl part has from 1 to 6 carbon atoms;

aliphatic acylamino groups having from 1 to 6 carbon atoms; aromatic acrylamino groups in which the aromatic part is a carbocyclic aryl group which has from 6 to 10 ring carbon atoms and which is unsubstituted or is substituted by at least one substituent selected from substituents C, defined below; nitro groups; and carboxy groups;

said substituents C are selected from: alkyl groups having from 1 to 6 carbon atoms; alkoxy groups having from 1 to 6 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; cyano groups; nitro groups; and carboxy groups.

Compounds of formula V and methods of preparing compounds of formula V are described in European Patent Application Publication Number 0567271 A2, published Oct. 27, 1993. Said compounds are disclosed therein as being useful in inhibiting steroid 5α-reductase.

As used herein, unless otherwise specified, $C_{1-n}$alkyl and $C_{1-n}$alk means a straight or branched hydrocarbon chain having 1 to n carbons and alk means a straight or branched hydrocarbon chain having 1 to 12 carbons.

Preferably the substituted 3,5-diene steroidal compound for use in the presently invented stabilized tablet formations and presently invented methods is N-t-butyl-androst-3,5-diene-17β-carboxamide-3-carboxylic acid. N-t-butyl-androst-3,5-diene-17β-carboxamide-3-carboxylic acid can be prepared as described in U.S. Pat. No. 5,017,568. This compound is disclosed therein as being useful in inhibiting steroid 5αreductase.

Although stable when blended or granulated with one or more commonly used pharmaceutical excipients such as, for example, lactose, tribasic calcium phosphate, silicon dioxide, corn starch, sodium starch glycolate, hydroxypropyl cellulose, hydroxypropyl methylcellulose, gelatin, magnesium stearate, microcrystalline cellulose, mannitol, and sorbitol, substituted 3,5-diene steroidal compounds were unexpectedly found to undergo a significant increase in the rate of formation of degradation products when compressed into tablets with such pharmaceutical excipients. This increase in degradation products occurs whether the substituted 3,5-diene steroidal compound and said excipients are formulated in direct compression tablets or in wet granulation tablets.

As used herein, unless otherwise indicated, the term "tablet" and derivatives thereof, means a direct compression tablet or a wet granulation tablet.

The reduction of degradation products of steroidal compounds in pharmaceutical formulations is of particular importance because minor changes in the structure of steroids are known to produce profound changes in its biological ativity. Moreover, steroidal compounds are known to be extremely potent, often requiring only very low doses of the compound to exhibit pharmaceutical activity.

It has now been found that the addition of a fatty acid, preferably stearic acid or palmitic acid; an antioxidant, preferably butylated hydroxyanisol (BHA) or butylated hydroxytoluene (BHT), most preferably BHT; or a combination of a fatty acid and an antioxidant, to a blend of pharmaceutical excipients containing a substituted 3,5-diene steroidal compound dramatically decreases the percentage of degradation products of the active in subsequently compressed tablets. Said tablets are prepared by compression under normal operating conditions using a standard tablet press.

The stability of N-t-butyl-androst-3,5-diene-17β-carboxamide-3-carboxylic acid (compound A) in various tablet formulations was determined by HPLC analysis. Degradation products were analyzed by LC/MS and unexpectedly found to be the result of oxidative additions (the 7 keto oxidation product and others) which only occurred when blends or granulations of Compound A were compressed into tablets. In order to reduce the percentage of degradation products to desired levels, preferably an increase of no more than 0.2 percent from baseline at day 0 after two weeks in the Accelerated Stability Screening Method (described herein), numerous tablet formulations were prepared and analyzed as indicated below.

In order to facilitate research efforts an Accelerated Stability Screening Method was developed. It was found that storing tablets at 85° C. for a short time (preferably two weeks) is suitable for predicting long term stability at room temperature. This method was employed upon noting that the degradation profiles generated at room temperature as compared to 85° C. were slmilar and that the profiles generated for tablets prepared by either direct compression (dry granulation process) or fluid bed granulation (wet granulation process) are the same.

Direct Compression Tablets

Experiments 1 and 2 were performed (utilizing Compound A) in order to determine the most advantageous direct compression tablet formulations of substituted 3,5-diene steroidal compounds.

Experiment 1

In Experiment 1 Compound A, microcrystalline cellulose, lactose, corn starch and sodium starch glycolate shown in Table I below, were mixed in the proportions shown. The mixture was split in half (into Batch 1 and Batch 2). Batch 1 was mixed with 1 percent magnesium stearate and compressed into appropriately sized tablets preferably 300 mg to 350 mg tablets each containing from about 80 mg to 85 mg of active compound (no stearic acid group). Batch 2 was first mixed and granulated with 2 percent stearic acid, then mixed and granulated with 1 percent magnesium stearate and compressed into appropriatly sized tablets preferably 300 mg to 350 mg tablets each containing from about 80 mg to 85 mg of active compound (stearic acid group). The tablets thus prepared were placed in stability chamber at 85° and the results of the stability test were recorded in Table 2 below.

TABLE 1

|  |  | % w/w |
|---|---|---|
| Batch 1 | Compound A | 10 |
|  | Microcrystalline Cellulose | 40 |
|  | Lactose | 32 |
|  | Corn Starch | 10 |
|  | Sodium Starch Glycolate | 7 |
|  | Mg Stearate | 1 |
| Batch 2 | Compound A | 10 |
|  | Microcrystalline Cellulose | 40 |
|  | Lactose | 32 |
|  | Corn Starch | 10 |
|  | Sodium Starch Glycolate | 7 |
|  | Stearic Acid | +2 |
|  | Mg Stearate | 1 |

TABLE 2

|  | % Degradation Day 0 | % Degradation Day 4 | % Degradation Day 11 |
|---|---|---|---|
| Batch 1 (No Stearic Acid) | 0 | 0.05 | 0.17 |
| Batch 2 (Stearic Acid) | 0 | 0.01 | 0.01 |

Experiment 2

In Experiment 2 one gram of Compound A was mixed and granulated with ten grams of lactose. The mixture was split into three equal parts (Batch 3 Batch 4 and Batch 5). Batch 3 was compressed into tablets of about 300 mg to 350 mg, about 30 mg to 35 mg of active compound (Control group: no additives). Batch 4 was mixed with two percent pure stearic acid and compressed into tablets of about 300 mg to 350 mg, about 30 mg to 35 mg of active compound. Batch 5 was mixed with two percent pure palmitic acid and compressed into tablets of about 300 mg to 350 mg, about 30 mg to 35 mg of active compound. The tablets thus prepared were placed in stability chamber at 85° C. and the results of the stability test were recorded in Table 3 below.

TABLE 3

|  | % Degradation Day 0 | % Degradation Day 6 | % Degradation Day 11 |
|---|---|---|---|
| Batch 3 (Control) | 0 | 0.47 | 0.54 |
| Batch 4 (Pure Stearic Acid) | 0 | 0.03 | 0.04 |
| Batch 5 (Pure Palmitic Acid) | 0 | 0.08 | 0.11 |

Wet Granulation Process

Experiments 3 to 6 were performed (utilizing Compound A) in order to determine the most advantageous wet granulation tablet formulations of substituted 3,5-diene compounds. To perform the wet granulation experiments a 'Standard Granulation' containing Compound A was utilized. To prepare the Standard Granulation Compound A (generally about 37% of this mixture) and lactose (generally about 57% of this mixture) are mixed and granulated with about a 9% solution of hydroxypropylmethyl cellulose (generally about 6% of this mixture). The wet granules are screened and dried to form the Standard Granulation.

Experiment 3

In Experiment 3 Standard Granulation, corn starch, sodium starch glycolate, microcrystalline cellulose, magnesium stearate and stearic acid (for Batch 6) or additional magnesium stearate (for Batch 7) shown in Table 4 below, were blended in the proportions shown and compressed into tablets of about 300 mg to 350 mg, about 80 mg to 85 mg of active compound. The tablets thus prepared were placed in stability chamber at 85° C. and the results of the stability test were recorded in Table 5 below.

TABLE 4

| Batch 6 | |
|---|---|
| Standard Granulation | 715 g |
| Stearic Acid | 23 g |
| Corn Starch | 49.5 g |
| Sodium Starch Glycolate | 50 g |
| Microcrystalline Cellulose | 150 g |
| Magnesium Stearate | 12.5 g |
| Batch 7 | |
| Standard Granulation | 715 g |
| Stearic Acid | 23 g |
| Corn Starch | 49.5 g |
| Sodium Starch Glycolate | 50 g |
| Microcrystalline Cellulose | 150 g |
| Magnesium Stearate | 12.5 g |

TABLE 5

| Batch 6 | % Degradation Day 0 | % Degradation Day 11 |
|---|---|---|
| Batch 6 | 0 | 0.13 |
| Batch 7 | 0 | 0.31 |

Experiment 4

In Experiment 4 Standard Granulation and BHT (for Batch 8) shown in Table 6 below, or stearic acid and BHT (for Batch 9) shown in Table 7 below, were mixed and granulated in the proportions shown and compressed into tablets of about 350 mg total tablet weight. The tablets thus prepared were placed in stability chamber at 85° C. and the results of the stability test were recorded in Tables 6 and 7 below.

TABLE 6

| Batch 8 % w/w BHT | % Degradation Day 0 | % Degradation Day 14 |
|---|---|---|
| 0 | 0 | 0.57 |
| 0.1 | 0 | 0.22 |
| 0.5 | 0 | 0.45 |
| 1.0 | 0 | 0.17 |
| 2.0 | 0 | 0.10 |

TABLE 7

| Batch 9 % w/w Stearic Acid | % w/w BHT | % Degradation Day 0 | % Degradation Day 14 |
|---|---|---|---|
| 0.2 | 0.1 | 0 | 0.34 |
| 1.0 | 0.5 | 0 | 0.04 |
| 2.0 | 1.0 | 0 | 0.02 |
| 4.0 | 2.0 | 0 | 0.03 |

Experiment 5

In Experiment 5 Standard Granulation (at about 72% w/w), microcrystalline cellulose (from 14% to 17% w/w depending on BHT and stearic acid content from Table 8) corn starch (at about 5% w/w), sodium starch glycolate (at about 5% w/w) and stearic acid and BHT (for Batch 10) shown in Table 8 below, were mixed and granulated in the proportions shown and compressed into 300 mg tablets (about 80 mg of Compound A). The tablets thus prepared were placed in stability chamber at 85° C. and the results of the stability test were recorded in Table 8 below.

TABLE 8

| Batch 10 % w/w Stearic Acid | % w/w BHT | % Degradation Day 0 | % Degradation Day 15 |
|---|---|---|---|
| 0 | 0 | 0 | 0.75 |
| 0 | 0 | 0 | 0.59 |
| 0.5 | 0.25 | 0 | 0.1 |
| 1.0 | 0.52 | 0 | 0 |
| 1.6 | 0.79 | 0 | 0.03 |
| 2.0 | 1.05 | 0 | 0.01 |
| 2.0 | 1.05 | 0 | 0.03 |

Experiment 6

In Experiment 6 Standard Granulation (at about 72% w/w), microcrystalline cellulose (from 16% to 17% w/w depending on BHT content from Table 9), corn starch (at about 5% w/w), sodium starch glycolate (at about 5%) magnesium stearate (at about 1%), stearic acid (at about 2%) and BHT (for Batch 11) shown in Table 9 below, were mixed and granulated in the proportions shown and compressed into 300 mg tablets (about 80 mg of Compound A). The tablets thus prepared were placed in stability chamber at 85° C. and the results of the stability test were recorded in Table 9 below.

TABLE 9

| Batch 11 % w/w BHT | % Degradation Day 0 | % Degradation Day 7 | % Degradation Day 16 |
|---|---|---|---|
| 0 | 0 | 0.12 | 0.19 |
| 0.1 | 0 | 0 | 0 |
| 0.25 | 0 | 0 | 0 |
| 0.5 | 0 | 0 | 0 |
| 1.0 | 0 | 0.01 | 0.03 |

The data from the above experiments demonstrates the ability of the presently discovered invention to stabilize direct compression tablets and wet granulation tablets containing substituted 3,5-diene steroidal compounds.

Fatty acids, particularly stearic acid, are known pharmaceutical excipients which are utilized in the art, primarily as tablet lubricants. Stearic acid, as a tablet lubricant, is considered interchangeable with other known tablet lubricants, particularly magnesium stearate. As discovered herein, fatty acids are disclosed as exhibiting the previously unknown ability to stabilize tablet formulations of substituted 3,5-diene steroidal compounds when other known tablet lubricants, particularly magnesium stearate, and other known pharmaceutical excipients do not exhibit such activity. As such, the present invention also relates to the use of fatty acids, preferably stearic acid or palmitic acid, most preferably stearic acid, as stabilizing agens in tablet formulations, particularly tablet formulations of substituted 3,5-diene steroidal compounds.

Preferably the fatty acid will be present in the finished tablet, as prepared herein, in an amount from about 0.5% to about 10% by weight.

Most preferably the fatty acid will be present in the finished tablet, as prepared herein, in an amount from about 1% to about 3% by weight, most preferably about 2%.

By the term "stabilized", and derivatives thereof, as used herein is meant that the subject substituted 3,5-diene steroidal compound when compressed into a tablet, under normal operating conditions using a standard tablet press, with a blend of pharmaceutical exeipients and a fatty acid, an antioxidant or a combination of a fatty acid and an antioxidant will experience the formation of less degradation products, preferably less than one half of the degradation products, experienced by said substituted 3,5-diene steroidal compound when compressed into a tablet with the same blend of pharmaceutical excipients without such fatty acid, such antioxidant or such combination of a fatty acid and an antioxidant. Assessing the ability of a fatty acid, an antioxidant or a combination of a fatty acid and an antioxidant to stabilize a particular substituted 3,5-diene steroidal compound is accomplished by comparing the stability of tablets containing a blend of pharmaceutical excipients, the subject substituted 3,5-diene steroidal compound and such fatty acid, such antioxidant or such combination of a fatty acid and an antioxidant to tablets wherein the only difference is that said fatty acid, said antioxidant or said combination of a fatty acid and an antioxidant is left out (as in Experiment 1) or substituted for by another pharmaceutical excipient, such as magnesium stearate (as in Experiment 3).

This invention provides for a method of stabilizing tablet formulations of substituted 3,5-diene steroidal compounds which comprises:

(a) admixing a fatty acid, an antioxidant or a combination of a fatty acid and an antioxidant with a pharmaceutical excipient blend and a substituted 3,5-diene steroidal compound;

(b) compressing the resulting mixture into tablets.

This invention also provides for a pharmaceutical formulation in tablet form comprising: a pharmaceutical excipient blend, a substituted 3,5-diene steroidal compound and a fatty acid, an antioxidant or a combination of a fatty acid and an antioxidant, preferably stearic acid for a direct compression tablet; preferably a combination of stearic acid and BHT for a wet granulation tablet.

By the term "pharmaceutical excipient blend" and derivatives thereof, as used herein is meant a mixture, a granulation or an admix of a mixture and a granulation of a plurality of commonly used pharmaceutical excipients, such as lactose, tribasic calcium phosphate, silicon dioxide, corn starch, sodium starch glycolate, hydroxypropyl cellulose, hydroxypropyl methylcellulose, gelatin, magnesium stearate, microcrystalline cellulose, mannitol or sorbitol, excluding fatty acids and antioxidants. Preferably when a pharmaceutical excipient blend, as defined herein, is utilized in a granulation, said granulation will also contain a substituted 3,5-diene steroidal compound.

In the presently invented methods and in the presently invented tablet formulations preferred antioxidants for use herein are butylated hydroxyanisol (BHA) and butylated hydroxytoluene (BHT), most preferably BHT, preferably in an amount of from about 0.05% to about 2% by weight, more preferably from about 0.1% to about 1% by weight, most preferably about 0.25% by weight.

Contemplated equivalents of substituted 3,5-diene steroidal compounds for use herein are compounds of the formula:

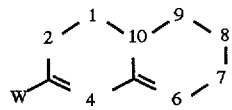

wherein W is an electron-withdrawing group; and the $C_1$ and $C_2$ positions and the $C_8$ to $C_{10}$ positions are optionally substituted with pharmaceutically acceptable substituents, degrees of unsaturation, a combination of pharmaceutically acceptable substituents and degrees of unsaturation or form part of a larger multicyclic compound.

Without further elaboration, it is believed that one skilled in the art can, using the preceding description, utilize the present invention to its fullest extent. The following Examples are, therefore, to be construed as merely illustrative and not a limitation of the scope of the present invention.

All of the excipients utilized herein are standard pharmaceutical grade excipients available from numerous manufactures well known to those in the art, except that pure stearic acid and pure palmitic acid (from Experiment 2), are not considered pharmaceutical grade and were obtained from the Aldrich Chemical Company Milwaukee, Wis. Standard grade pharmaceutical excipients, from any reputable source, are considered suitable for use herein.

EXAMPLE 1 dry granulation process

The lactose, microcrystalline cellulose, sodium starch glycolate, stearic acid, magnesium stearate and N-t-butyl-androst-3,5-diene-17β-carboxamide-3-carboxylic acid shown in Table 10 below, are blended in the proportions shown. The dry granules are screened and compressed into tablets. Said tablets are optionally coated with, for example, a film coat. The procedure of Example I will produce approximately 750,000 tablets of approximately 133 mg each containing about 20 mg of the active ingredient.

TABLE 10

| Ingredients | Amounts |
|---|---|
| N-t-butyl-androst-3,5-diene-17β-carboxamide-3-carboxylic acid | 15,000 g |
| Microcrystalline Cellulose | 15,000 g |
| Lactose | 62,500 g |
| Sodium Starch Glycolate | 5,000 g |
| Stearic Acid | 2,000 g |
| Magnesium Stearate | 500 g |

EXAMPLE 2 wet granulation process

The lactose; sodium starch glycolate; microcrystalline cellulose; and N-t-butyl-androst-3,5-diene-17β-carboxamide-3carboxylic acid shown in Table 11 below, are mixed and granulated in the proportions shown with a 9% solution of the hydroxypropylmethyl cellulose. The wet granules are screened, dried, mixed with the stearic acid; magnesium stearate and butylated hydroxytoluene, screened and compressed into tablets. Said tablets axe optionally coated with for example a film coat. The procedure of Example 2 will produce approximately 374,000 tablets of approximately 267 mg each containing about 80 mg of the active ingredient.

TABLE 11

| Ingredients | Amounts |
|---|---|
| N-t-butyl-androst-3,5-diene-17β-carboxamide-3-carboxylic acid | 30,000 g |
| Lactose | 25,000 g |
| Sodium Starch Glycolate | 5,000 g |
| Microcrystalline Cellulose | 32,000 g |
| Hydroxypropylmethyl Cellulose | 4,000 g |
| Stearic Acid | 3,000 g |
| Magnesium Stearate | 500 g |
| Butylated hydroxytoluene | 500 g |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of preparing stabilized tablet formulations of substituted 3,5-diene steroidal compounds wherein the improvement comprises, the process of reducing the significant increase in the rate of formation of degradation products formed from substituted 3,5-diene steroidal compounds whether compressed into tablets by wet granulation or by direct compression, with commonly used pharmaceutical excipients which consists essentially of the step of directly compressing said substituted 3,5-diene steroidal compound admixed with (A) from about 0.05% to about 2% by weight of butylated hydroxyonisol or butylated hydroxytoluene, as antioxidant, and (B) from about 1% to about 3% by weight of stearic acid or palmitic acid, as stabilizing tablet lubricant.

2. A pharmaceutical formulation produced in accordance with the dried compression tabletting process of claim 1.

* * * * *